US012622746B2

(12) United States Patent
Smail

(10) Patent No.: US 12,622,746 B2
(45) Date of Patent: May 12, 2026

(54) APPARATUS AND METHODS FOR REDUCING MICROBUBBLES FORMATION DURING CARDIAC ABLATION

(71) Applicant: Boston Scientific Scimed Inc., Maple Grove, MN (US)

(72) Inventor: El Yacine Alex Smail, Vaudreuil-Dorion (CA)

(73) Assignee: Boston Scientific Scimed, Inc., Maple Grove, MN (US)

( * ) Notice: Subject to any disclaimer, the term of this patent is extended or adjusted under 35 U.S.C. 154(b) by 964 days.

(21) Appl. No.: 17/748,019

(22) Filed: May 18, 2022

(65) Prior Publication Data

US 2022/0370122 A1     Nov. 24, 2022

Related U.S. Application Data

(60) Provisional application No. 63/191,134, filed on May 20, 2021.

(51) Int. Cl.
A61B 18/14 (2006.01)
A61B 18/00 (2006.01)
(52) U.S. Cl.
CPC ...... *A61B 18/1492* (2013.01); *A61B 2018/00577* (2013.01); *A61B 2018/00613* (2013.01); *A61B 2018/1405* (2013.01)
(58) Field of Classification Search
CPC ...... A61B 18/1492; A61B 2018/00577; A61B 2018/1405; A61N 2007/0043
See application file for complete search history.

(56) References Cited

U.S. PATENT DOCUMENTS

2002/0022833 A1*  2/2002  Maguire ............ A61B 17/2202
                                                          606/41
2009/0287205 A1    11/2009  Ingle
                        (Continued)

FOREIGN PATENT DOCUMENTS

EP       2696773 B1     6/2017
EP       3495018 A1     6/2019
WO    2017003853 A1     1/2017

OTHER PUBLICATIONS

International Search Report and Written Opinion Issued in PCT/US2022/029926, mailed Aug. 25, 2022.
                        (Continued)

*Primary Examiner* — Joseph A Stoklosa
*Assistant Examiner* — Annie L Shoulders
(74) *Attorney, Agent, or Firm* — Nelson Mullins Riley & Scarborough LLP

(57)            ABSTRACT
Various aspects of the present disclosure are directed towards apparatuses, systems, and methods for electroporation ablation. The electroporation ablation catheter may include an electrode assembly comprising one or more electrodes configured to generate electric fields in target tissue in response to a plurality of electrical pulse sequences delivered in a plurality of therapy sections, and an ultrasound transducer configured to generate a first set of ultrasound signals during a first electrical pulse sequence of the plurality of electrical pulse sequences and generate a second set of ultrasound signals after an end of the first electrical pulse sequence and before a beginning of a second electrical pulse sequence, the second electrical pulse sequence being an electrical pulse sequence subsequent to the first electrical pulse sequence.

18 Claims, 7 Drawing Sheets

(56) References Cited

U.S. PATENT DOCUMENTS

2017/0000553 A1*   1/2017  Wiener .............. A61B 18/1233
2017/0065339 A1*   3/2017  Mickelsen ............. A61N 1/327
2022/0071694 A1*   3/2022  Govari ................... A61B 5/287
2022/0401146 A1*  12/2022  Asconeguy ............ A61B 5/349
2023/0414299 A1*  12/2023  Khuri-Yakub ........ B06B 1/0215

OTHER PUBLICATIONS

McDannold, et al., "Blood-brain barrier disruption induced by focused ultrasound and circulating preformed microbubbles appears to be characterized by the mechanical index," Ultrasond Med Biol., vol. 34 and No. 5, May 2008, pp. 834-840.
Kern, et al., "Ultrasound Microbubble Destruction Imaging in Acute Middle Cerebral Artery Stroke," Stroke, Jul. 2004, pp. 1665-1670.
Tu, et al., "Ultrasound-mediated microbubble destruction: a new method in cancer immunotherapy," Onco Targets and Therapy, vol. 11, 2018, pp. 5763-5775.

* cited by examiner

500

505 — Dispose an electroporation catheter proximate to target tissue

510 — Generate an electric field proximate to the target tissue

515 — Generate a first set of ultrasound signals

520 — Generate a second set of ultrasound signals

1

APPARATUS AND METHODS FOR REDUCING MICROBUBBLES FORMATION DURING CARDIAC ABLATION

CROSS REFERENCE TO RELATED APPLICATION

This application claims priority to Provisional Application No. 63/191,134, filed May 20, 2021, which is herein incorporated by reference in its entirety.

TECHNICAL FIELD

The present disclosure relates to medical apparatus, systems, and methods for reducing or preventing microbubbles during cardiac ablation by irreversible electroporation.

BACKGROUND

Ablation procedures are used to treat many different conditions in patients. Ablation may be used to treat cardiac arrhythmias, benign tumors, cancerous tumors, and to control bleeding during surgery. Usually, ablation is accomplished through thermal ablation techniques including radiofrequency (RF) ablation and cryoablation. In RF ablation, a probe is inserted into the patient and radio frequency waves are transmitted through the probe to the surrounding tissue. The radio frequency waves generate heat, which destroys surrounding tissue and cauterizes blood vessels. In cryoablation, a hollow needle or cryoprobe is inserted into the patient and cold, thermally conductive fluid is circulated through the probe to freeze and kill the surrounding tissue. RF ablation and cryoablation techniques indiscriminately kill tissue through cell necrosis, which may damage or kill otherwise healthy tissue, such as tissue in the esophagus, phrenic nerve cells, and tissue in the coronary arteries.

Another ablation technique uses electroporation. In electroporation, or electro-permeabilization, an electric field is applied to cells to increase the permeability of the cell membrane. The electroporation may be reversible or irreversible, depending on the strength of the electric field. If the electroporation is reversible, the increased permeability of the cell membrane may be used to introduce chemicals, drugs, and/or deoxyribonucleic acid (DNA) into the cell, prior to the cell healing and recovering. If the electroporation is irreversible, the affected cells are killed through apoptosis.

Irreversible electroporation (IRE) may be used as a nonthermal ablation technique. In IRE, trains of short, high voltage pulses are used to generate electric fields that are strong enough to kill cells through apoptosis. In ablation of cardiac tissue, IRE may be a safe and effective alternative to the indiscriminate killing of thermal ablation techniques, such as RF ablation and cryoablation. IRE may be used to kill target tissue, such as myocardium tissue, by using an electric field strength and duration that kills the target tissue but does not permanently damage other cells or tissue, such as non-targeted myocardium tissue, red blood cells, vascular smooth muscle tissue, endothelium tissue, and nerve cells.

In some IRE procedures, there is a possibility of microbubble forming during the treatment of the patient. The formation of microbubbles can cause tissue damage and increase risk for treatment of the patient. A way to prevent the formation of microbubbles during IRE procedures is needed.

SUMMARY

In Example 1, an electroporation ablation catheter comprises an electrode assembly. The electrode assembly comprises one or more electrodes configured to generate electric fields in target tissue in response to a plurality of electrical pulse sequences delivered in a plurality of therapy sections, and an ultrasound transducer configured to generate a first set of ultrasound signals during a first electrical pulse sequence of the plurality of electrical pulse sequences and generate a second set of ultrasound signals after an end of the first electrical pulse sequence and before a beginning of a second electrical pulse sequence, the second electrical pulse sequence being an electrical pulse sequence subsequent to the first electrical pulse sequence, wherein the first set of ultrasound signals has a first average magnitude, the second set of ultrasound signals has a second average magnitude, and the first average magnitude is different from the second average magnitude.

In Example 2, the electroporation ablation catheter of Example 1, wherein the first average magnitude is lower than the second average magnitude.

In Example 3, the electroporation ablation catheter of Example 1 or 2, wherein the electrode assembly further comprises an internal component disposed at an interior cavity of the electrode assembly, and the ultrasound transducer is disposed on the internal component.

In Example 4, the electroporation ablation catheter of any of Examples 1-3, further comprising one or more wirings to power up the ablation catheter and to control at least one of a magnitude and frequency of the first set and the second set of ultrasound signals.

In Example 5, the electroporation ablation catheter of any of Examples 1-4, wherein the electrode assembly further comprises a plurality of splines, and wherein the ultrasound transducer comprises one ultrasound transducer disposed on one of the plurality of splines.

In Example 6, the electroporation ablation catheter of any of Examples 1-5, wherein the first set of ultrasound signals has a first average frequency, wherein the second set of ultrasound signals has a second average frequency, wherein the first average frequency is different from the second average frequency.

In Example 7, an electroporation ablation catheter comprises an electrode assembly. The electrode assembly comprises one or more electrodes configured to generate electric fields in target tissue in response to a plurality of electrical pulse sequences delivered in a plurality of therapy sections, an ultrasound transducer configured to generate ultrasound signals, and an internal component disposed at an interior cavity of the electrode assembly, wherein the ultrasound transducer is disposed on the internal component.

In Example 8, the electroporation ablation catheter of Example 7, wherein the ultrasound transducer is further configured to generate a first set of ultrasound signals during a first electrical pulse sequence of the plurality of electrical pulse sequences and generate a second set of ultrasound signals after an end of the first electrical pulse sequence and before a beginning of a second electrical pulse sequence, the second electrical pulse sequence being an electrical pulse sequence subsequent to the first electrical pulse sequence.

In Example 9, the electroporation ablation catheter of any of Examples 7-8, wherein the first set of ultrasound signals has a first average magnitude, the second set of ultrasound signals has a second average magnitude.

In Example 10, the electroporation ablation catheter of Example 9, wherein the first average magnitude is different from the second average magnitude.

In Example 11, the electroporation ablation catheter of any of Examples 7-10, wherein the first average magnitude is lower than the second average magnitude.

3

In Example 12, the electroporation ablation catheter of any of Examples 7-11, wherein the internal component comprises a deployment shaft.

In Example 13, the electroporation ablation catheter of any of Examples 7-12, further comprising a catheter shaft having a proximal end and a distal end, wherein the electrode assembly extends from the distal end of the catheter shaft, and wherein the deployment shaft extends from the distal end of the catheter shaft.

In Example 14, the electroporation ablation catheter of Example 7, wherein the electrode assembly further comprises a plurality of splines, and wherein the ultrasound transducer comprises one ultrasound transducer disposed on one of the plurality of splines.

In Example 15, the electroporation ablation catheter of Example 14, wherein the first set of ultrasound signals has a first average frequency, wherein the second set of ultrasound signals has a second average frequency, and wherein the first average frequency is different from the second average frequency.

In Example 16, an electroporation ablation catheter comprises an electrode assembly. The electrode assembly comprises one or more electrodes configured to generate electric fields in target tissue in response to a plurality of electrical pulse sequences delivered in a plurality of therapy sections, and an ultrasound transducer configured to generate a first set of ultrasound signals during a first electrical pulse sequence of the plurality of electrical pulse sequences and generate a second set of ultrasound signals after an end of the first electrical pulse sequence and before a beginning of a second electrical pulse sequence, the second electrical pulse sequence being an electrical pulse sequence subsequent to the first electrical pulse sequence, wherein the first set of ultrasound signals has a first average magnitude, the second set of ultrasound signals has a second average magnitude, and the first average magnitude is different from the second average magnitude.

In Example 17, the electroporation ablation catheter of Example 16, wherein the first average magnitude is lower than the second average magnitude.

In Example 18, the electroporation ablation catheter of Example 16, wherein the electrode assembly further comprises an internal component disposed at an interior cavity of the electrode assembly, and wherein the ultrasound transducer is disposed on the internal component.

In Example 19, the electroporation ablation catheter of Example 16, further comprising one or more wirings to power up the ablation catheter and to control at least one of a magnitude and frequency of the first set and the second set of ultrasound signals.

In Example 20, the electroporation ablation catheter of Example 16, wherein the electrode assembly further comprises a plurality of splines, and wherein the ultrasound transducer comprises one ultrasound transducer disposed on one of the plurality of splines.

In Example 21, the electroporation ablation catheter of Example 16, wherein the first set of ultrasound signals has a first average frequency, wherein the second set of ultrasound signals has a second average frequency, and wherein the first average frequency is different from the second average frequency.

In Example 22, an electroporation ablation catheter comprises an electrode assembly. The electrode assembly comprises one or more electrodes configured to generate electric fields in target tissue in response to a plurality of electrical pulse sequences delivered in a plurality of therapy sections, an ultrasound transducer configured to generate ultrasound signals, and an internal component disposed at an interior cavity of the electrode assembly, wherein the ultrasound transducer is disposed on the internal component.

In Example 23, the electroporation ablation catheter of Example 22, wherein the ultrasound transducer is further configured to generate a first set of ultrasound signals during a first electrical pulse sequence of the plurality of electrical pulse sequences and generate a second set of ultrasound signals after an end of the first electrical pulse sequence and before a beginning of a second electrical pulse sequence, the second electrical pulse sequence being an electrical pulse sequence subsequent to the first electrical pulse sequence.

In Example 24, the electroporation ablation catheter of Example 23, wherein the first set of ultrasound signals has a first average magnitude, the second set of ultrasound signals has a second average magnitude, and wherein the first average magnitude is different from the second average magnitude.

In Example 25, the electroporation ablation catheter of Example 24, wherein the first average magnitude is lower than the second average magnitude.

In Example 26, the electroporation ablation catheter of Example 22, wherein the internal component comprises a deployment shaft.

In Example 27, the electroporation ablation catheter of Example 26, further comprising a catheter shaft having a proximal end and a distal end, wherein the electrode assembly extends from the distal end of the catheter shaft, and wherein the deployment shaft extends from the distal end of the catheter shaft.

In Example 28, the electroporation ablation catheter of Example 22, wherein the electrode assembly further comprises a plurality of splines, and wherein the ultrasound transducer comprises one ultrasound transducer disposed on one of the plurality of splines.

In Example 29, the electroporation ablation catheter of Example 28, wherein at least a part of the plurality of splines form an interior cavity.

In Example 30, the electroporation ablation catheter of Example 23, wherein the first set of ultrasound signals has a first average frequency, wherein the second set of ultrasound signals has a second average frequency, wherein the first average frequency is different from the second average frequency.

In Example 31, a method of preventing microbubbles formation during cardiac ablation comprises disposing an electroporation catheter proximate to target tissue, the electroporation catheter comprising one or more electrodes and an ultrasound transducer, generating an electric field, by the one or more electrodes, in the target tissue in response to a plurality of electrical pulse sequences delivered in a plurality of therapy sections, the electric field having electric field strength sufficient to ablate the target tissue via irreversible electroporation, and generating, by the ultrasound transducer, a set of ultrasound signals.

In Example 32, the method of Example 31, wherein the set of ultrasound signals comprises a first set of ultrasound signals and a second set of ultrasound signals.

In Example 33, the method of Example 32, wherein the first set of ultrasound signals is generated during a first electrical pulse sequence of the plurality of electrical pulse sequences.

In Example 34, the method of Example 32, wherein the second set of ultrasound signals is generated after an end of the first electrical pulse sequence and before a beginning of a second electrical pulse sequence.

In Example 35, the method of Example 32, wherein the first set of ultrasound signals has a first average magnitude, wherein the second set of ultrasound signals has a second average magnitude, and wherein the first average magnitude is different from the second average magnitude.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
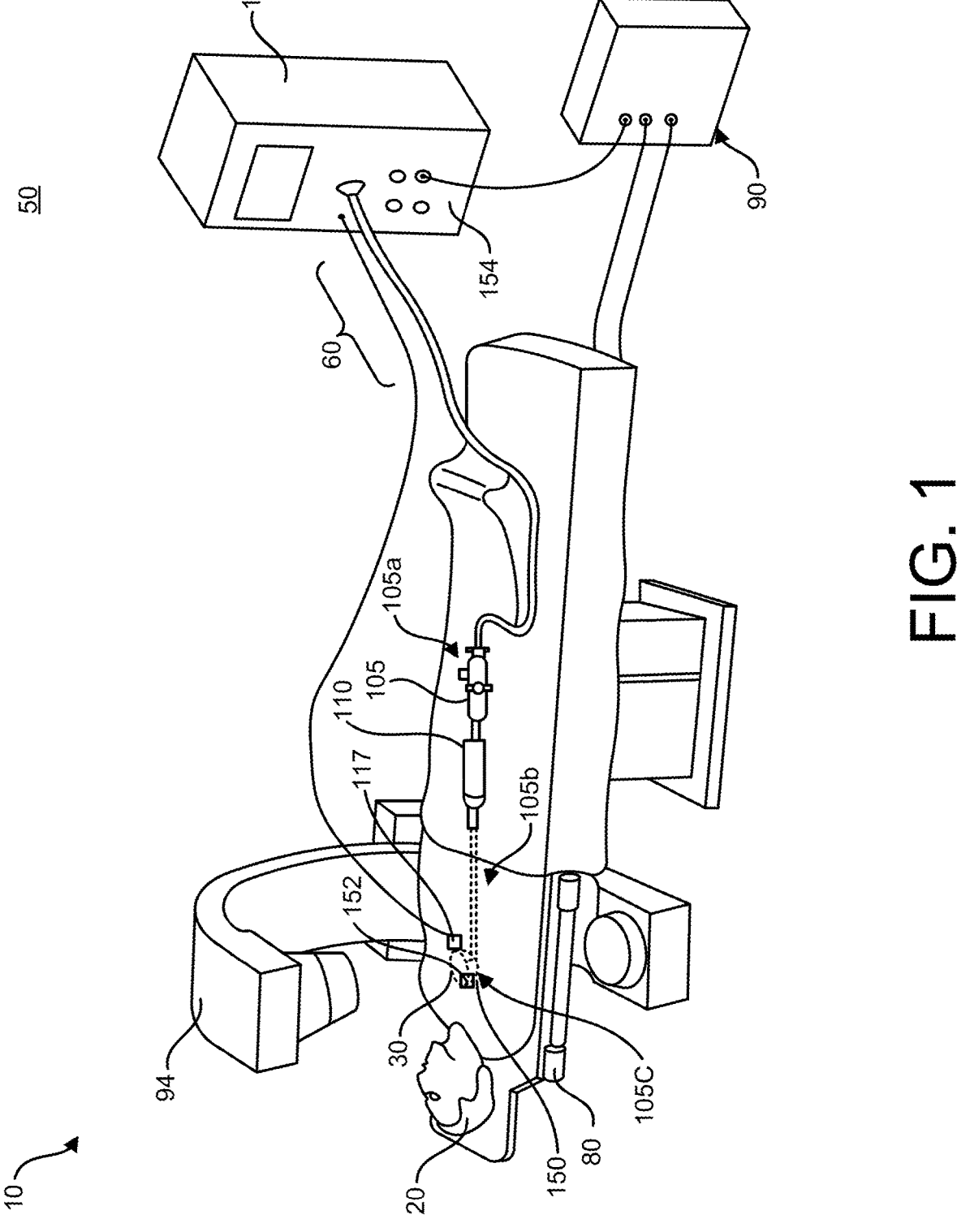
FIG. 1 is a diagram illustrating an exemplary clinical setting for treating a patient and for treating a heart of the patient, using an electrophysiology system, in accordance with embodiments of the subject matter of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although illustrative methods may be represented by one or more drawings (e.g., flow diagrams, communication flows, etc.), the drawings should not be interpreted as implying any requirement of, or particular order among or between, various steps disclosed herein. However, certain some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

Irreversible electroporation (IRE) uses high voltage, short (e.g., 100 microseconds or shorter) pulses to kill cells through apoptosis. IRE can be targeted to kill myocardium, sparing other adjacent tissues including the esophageal vascular smooth muscle and endothelium. During the course of IRE therapy sections, microbubbles may be formed. A therapy section may include a therapy bursts period and a quiet period. A therapy section (e.g., for a duration of around 10 milliseconds) may include a plurality of electrical pulses (e.g., 20 pulses, 30 pulses, etc.), also referred to as therapy bursts, generated and delivered continuously by an electroporation generator. The therapy burst period refers to the period of therapy bursts and the quiet period refers to the period without the therapy bursts. In some instances, the microbubbles may form during the quiet period. The formation of microbubbles can cause tissue damage and increase risk for treatment of the patient.

At least some embodiments of the present disclosure are directed to systems and methods to reduce, destruct, and/or prevent microbubbles formation during IRE ablation using ultrasonic technology. In some embodiments, an electroporation ablation system includes ultrasound transducer configured to generate ultrasound signals capable of microbubble destruction. In certain embodiments, the ultrasound transducers are configured to generate ultrasound signals with higher magnitude during the quiet periods (i.e. the period in between therapy bursts) than during the therapy bursts.

FIG. 1 is a diagram illustrating an exemplary clinical setting 10 for treating a patient 20, and for treating a heart 30 of the patient 20, using an electrophysiology system 50, in accordance with embodiments of the subject matter of the disclosure. The electrophysiology system 50 includes an ultrasound generator 154, an electroporation device 60, and an optional localization field generator 80. Also, the clinical setting 10 includes additional equipment such as imaging equipment 94 (represented by the C-arm) and various controller elements configured to allow an operator to control various aspects of the electrophysiology system 50. As will be appreciated by the skilled artisan, the clinical setting 10 may have other components and arrangements of components that are not shown in FIG. 1.

The electroporation device 60 includes an electroporation catheter 105, an introducer sheath 110, an electrode assembly 150, a controller 90, and an electroporation generator 130. In embodiments, the electroporation device 60 is configured to deliver electric field energy to target tissue in the patient's heart 30 to create tissue apoptosis, rendering the tissue incapable of conducting electrical signals. The controller 90 is configured to control functional aspects of the electroporation device 60. In embodiments, the controller 90 is configured to receive and send timing signals for the electroporation generator 130 to generate electrical pulses. In embodiments, the electroporation generator 130 is operable as a pulse generator for generating and supplying pulse sequences to the electroporation catheter 105. In embodiments, the electroporation generator 130 is operable to receive sensed signals from the accelerometer 117 and based on the received sensed signals act as a pulse generator for generating and supplying pulse sequences to the electroporation catheter 105.

In embodiments, the introducer sheath 110 is operable to provide a delivery conduit through which the electroporation catheter 105 may be deployed to the specific target sites within the patient's heart 30. It will be appreciated, however, that the introducer sheath 110 is illustrated and described herein to provide context to the overall electrophysiology system 50.

In the illustrated embodiment, the electroporation catheter 105 includes a handle 105a, a shaft 105b, and an electrode assembly 150, which is described further hereinafter. The handle 105a is configured to be operated by a user to position the electrode assembly 150 at the desired anatomical location. The shaft 105b has a distal end 105c and generally defines a longitudinal axis of the electroporation catheter 105. As shown, the electrode assembly 150 is located at or proximate the distal end 105c of the shaft 105b. In embodiments, the electrode assembly 150 is electrically coupled to the electroporation generator 130, to receive electrical pulse sequences or pulse trains, thereby selectively generating electrical fields for ablating the target tissue by irreversible electroporation.

In embodiments, as shown in FIG. 1, the electrode assembly 150 includes an ultrasound transducer 152 coupled to the ultrasound generator 154. In some examples, the ultrasound transducer 152 includes an ultrasonic piezo transducer. In some embodiments, the ultrasound generator 154 may be integrated into the electroporation generator 130. In embodiments, the ultrasound generator 154 may be separate from the electroporation generator 130. The controller 90 may be operably connected to the ultrasound generator 154, and may be configured to receive and to send timing signals for the ultrasound generator 154 to generate ultrasound waveforms according to timing signals received from the electroporation generator 130 (explained in more details below regarding FIG. 3). In embodiments, the ultrasound generator 154 is configured to generate ultrasound signals (described in further detail below) to reduce, destruct, and/or prevent microbubbles formation during IRE ablation. In some embodiments, the ultrasound generator 154 may be used to general ultrasound signals to reduce or prevent microbubbles formation. In some case, the ultrasound generator 154 may be controlled such that the ultrasound signals are generated in different amplitudes and/or frequencies between therapy burst periods and quiet periods of therapy sections.

The electroporation device 60 is operable to generate an IRE pulse sequence that includes a preconditioning (pre-treatment) pulse sequence and an electroporation pulse sequence. The IRE pulse sequence is configured to ablate target tissue. In embodiments, the preconditioning pulse sequence is a series of electrical pulses that ramp up in magnitude to tetanize skeletal muscle tissue and to provide electrolysis near target tissue. In embodiments, the electroporation pulse sequence is a series of electroporation pulses configured to cause irreversible damage to the target tissue.

In embodiments, the electroporation device 60 includes the accelerometer 117 that may be attached to the body of the patient 20, such as to the thorax of the patient, and electrically coupled to the electroporation generator 130. The accelerometer 117 is configured to sense contraction of the skeletal muscle system of the patient to detect tetany. The signals from the accelerometer 117 are received by the electroporation generator 130, which processes the signals to determine whether the skeletal muscle system of the patient is contracting and whether tetany has been achieved. In embodiments, the electroporation generator 130 is configured to provide the electroporation pulse sequence only after tetany has been achieved in the patient. In embodiments, the controller 90 is operable to receive sensed signals from the accelerometer 117 and based on the received sensed signals, control the electroporation generator 130 for generating and supplying pulse sequences to the electroporation catheter 105.

In embodiments, the electroporation device 60 acts as a closed system with the surface accelerometer 117 monitoring chest vibrations and the electroporation generator 130 modulating pulses until tetany is achieved and then the electroporation generator 130 delivers the electroporation pulses. Also, in embodiments, the local impedance of the target tissue and tissue surrounding the target tissue can be measured during this time to calculate pre-ablation and post-ablation values for evaluation of the lesion efficacy.

According to embodiments, various components (e.g., the controller 90) of the electrophysiological system 50 may be implemented on one or more computing devices. A computing device may include any type of computing device suitable for implementing embodiments of the disclosure. Examples of computing devices include specialized computing devices or general-purpose computing devices such as workstations, servers, laptops, portable devices, desktop, tablet computers, hand-held devices, general-purpose graphics processing units (GPGPUs), and the like, all of which are contemplated within the scope of FIG. 1 with reference to various components of the electrophysiological system 50.

In some embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices.

In some embodiments, the electrophysiological system 50 includes memory (not illustrated). The memory includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EE-PROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the memory stores computer-executable instructions for causing a processor (e.g., the controller 90) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

In some embodiments, the memory may include a data repository may be implemented using any one of the configurations described below. A data repository may include random access memories, flat files, XML files, and/or one or more database management systems (DBMS) executing on one or more database servers or a data center. A database management system may be a relational (RDBMS), hierarchical (HDBMS), multidimensional (MDBMS), object oriented (ODBMS or OODBMS) or object relational (OR-DBMS) database management system, and the like. The data repository may be, for example, a single relational database. In some cases, the data repository may include a plurality of databases that can exchange and aggregate data by data integration process or software application. In an exemplary embodiment, at least part of the data repository may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the electrophysiological system 50 can communicate via or be coupled to via a communication interface, for example, a wired or wireless interface. The communication interface includes, but not limited to, any wired or wireless short-range and long-range communication interfaces. The wired interface can use cables, umbilicals, and the like. The short-range communication interfaces may be, for example, local area network (LAN), interfaces conforming known communications standard, such as Bluetooth® standard, IEEE 802 standards (e.g., IEEE 802.11), a ZigBee® or similar specification, such as those based on the IEEE 802.15.4 standard, or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet.

Figure 2A:
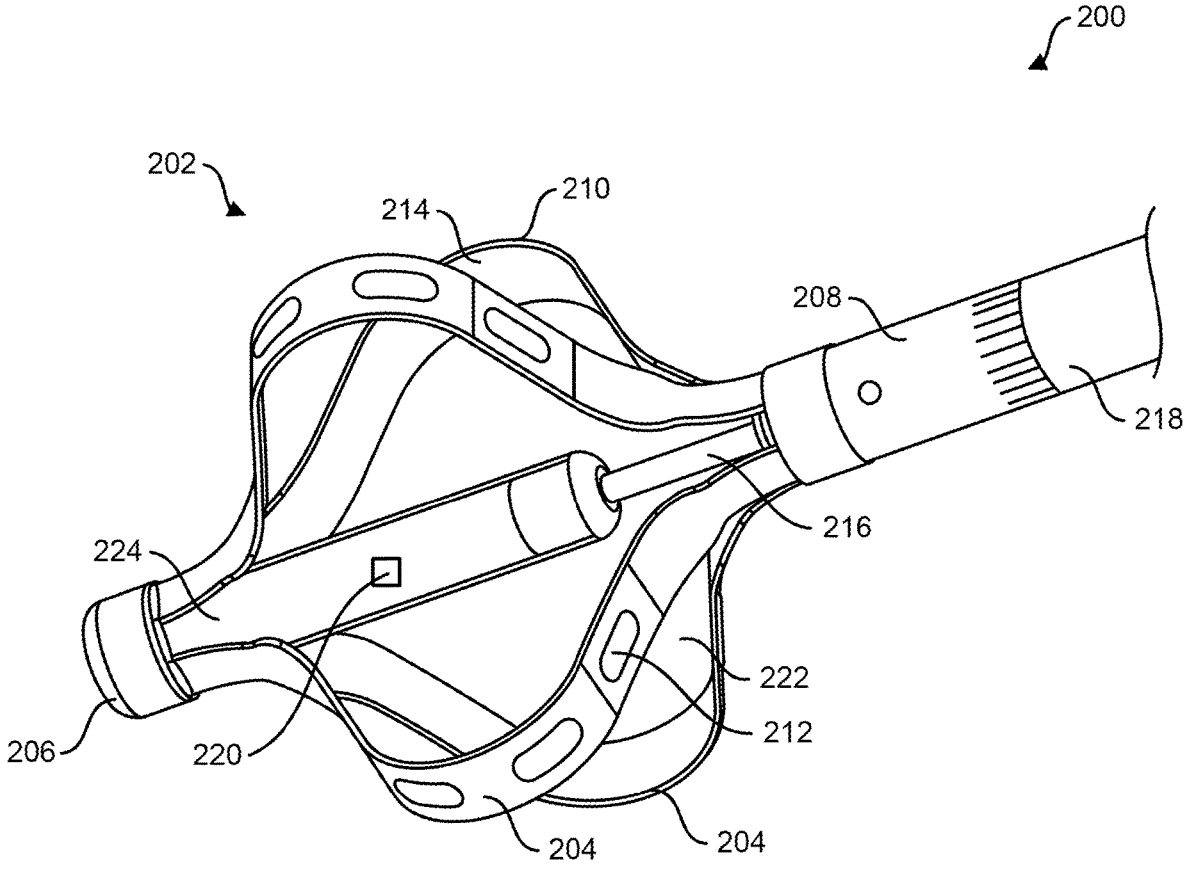
FIG. 2A is an exemplary electroporation ablation catheter comprising an ultrasound transducer, in accordance with embodiments of the subject matter of the disclosure.
Figure 2B:
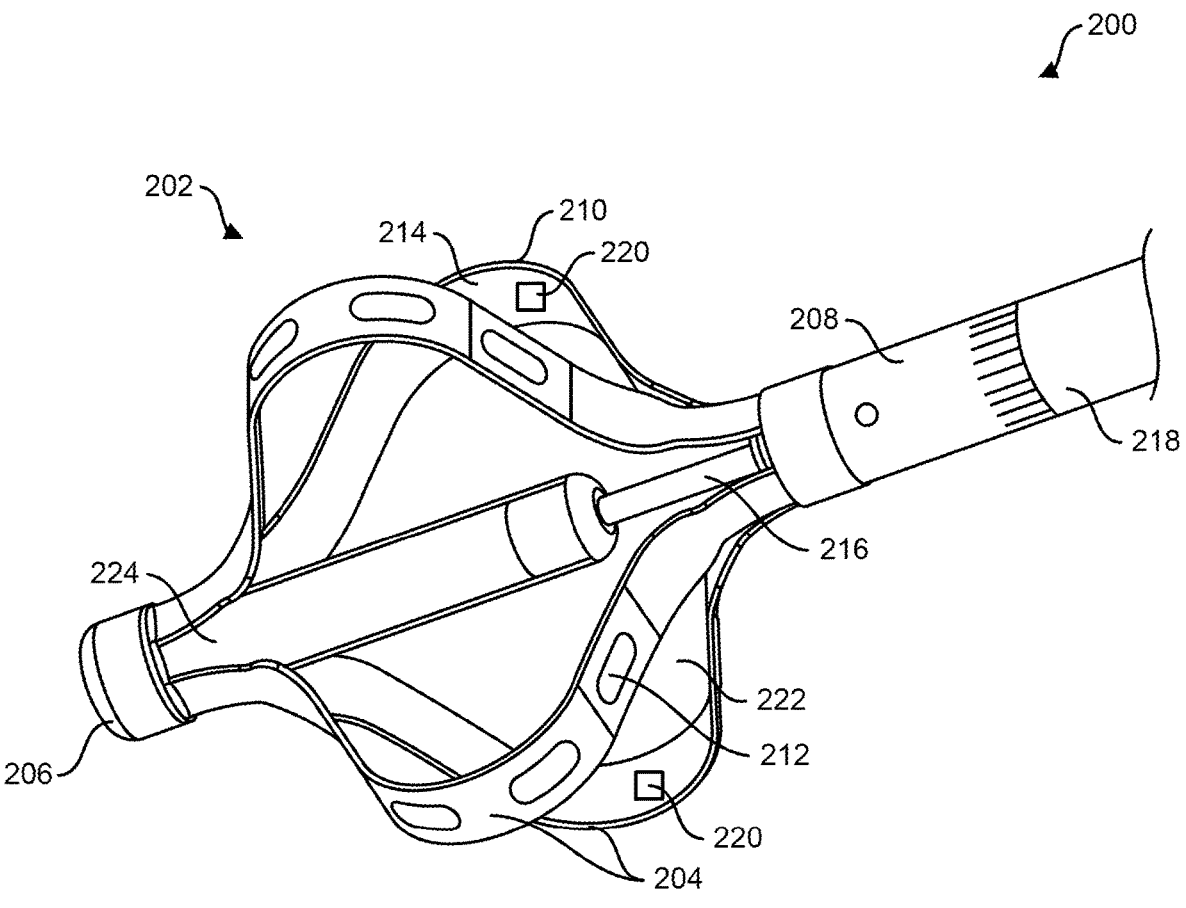
FIG. 2B is an exemplary electroporation ablation catheter comprising an ultrasound transducer, in accordance with embodiments of the subject matter of the disclosure.
Figure 2C:
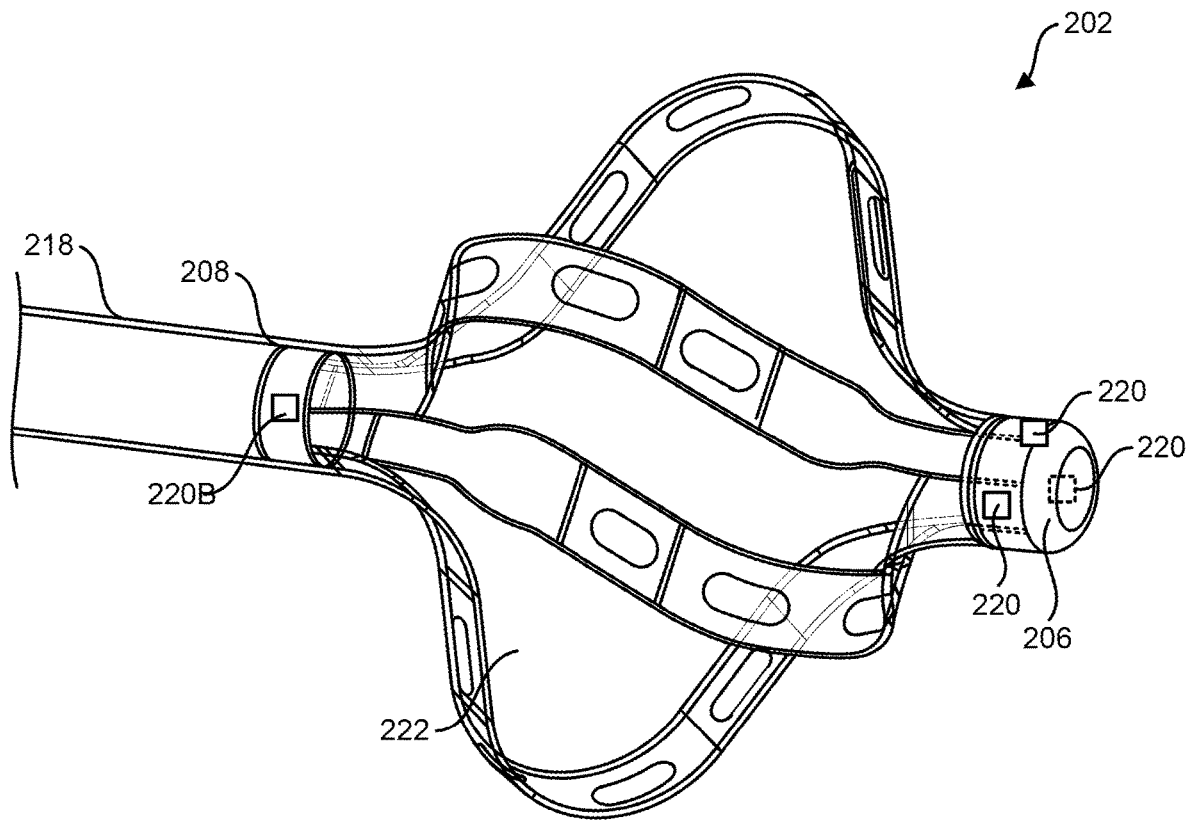
FIG. 2C is an exemplary electroporation ablation catheter comprising an ultrasound transducer, in accordance with embodiments of the subject matter of the disclosure.

FIGS. 2A-2C are partial perspective views showing the distal end of a cardiac mapping catheter 200, in accordance with embodiments of the subject matter of the disclosure. As shown in FIG. 2A, the electrode assembly 202 are deployed in a radially extended state. The electrode assembly 202 may include one or more splines 204 and an end cap 206. Each of the splines 204 may extend between the distal end 208 of the catheter 200 and the end cap 206, and forms an interior cavity 222. Each of the splines 204 may include a flexible polymer substrate 210 and a plurality of electrodes 212. In some embodiments, the flexible polymer substrate 210 may include a stiffening element 214. The stiffening element 214 may be, for example, a layer of nitinol. The stiffening element 214 may produce a force in each of the splines 204 that biases the electrode assembly 202 toward an undeployed state or configuration (not shown). In some embodiments, there may be 2-8 splines 204 connected to the distal end 208 of the catheter 200. In some embodiments, there may be more than 8 splines connected to the distal end 208 of the catheter 200.

In some embodiments, the electrodes 212 may be ablation electrodes, and are configured to generate electric fields in target tissue in response to a plurality of electrical pulse sequences delivered in a plurality of therapy sections. In some instances, at least a part of the one or more electrodes 212 are disposed on the one or more splines 204.

As shown in FIG. 2A, the deployment shaft 216 may extend from the end cap 206 and into the catheter body 218 at the distal end 208. In some embodiments, the end cap 206 may be an electrode for cardiac stimulation or tissue ablation. In some embodiments, the end cap 206 may contain a magnetic sensor for use in determining the location of the electrode assembly 202 within the body.

In some embodiments, the electrode assembly 202 includes an internal component 224 disposed at the interior cavity 222 of the electrode assembly 202. The deployment shaft 216 may be part of the internal component 224. In some embodiments, the electrode assembly further includes an ultrasound transducer 220 disposed on the internal component 224. The ultrasound transducer 220 may be used to destroy any microbubbles that may have formed as a result of the irreversible electroporation. During treatment, the ultrasound transducer 220, as a part of the electrode assembly 202, will be placed directly inside a liquid medium (i.e. blood or fluid within the patient's heart), where there will be a maximum absorption of the ultrasound signal.

The reflection coefficient (r) equals $(Z1-Z2)/(Z1+Z2)$, wherein Z1 is the acoustic impedance (resistance to the propagation of ultrasound waves through the tissue) near the transducer 220, and Z2 is the acoustic impedance near any bubble that may have formed during the treatment (not shown). Because Z1 and Z2 are relatively close in value, the power needed to destroy the bubbles is also relatively small. Moreover, as will be explained in more details below, we can further reduce and minimize the power needed for the transducer by synchronizing the ultrasound wave produced by the transducer with the burst train produced by the ablation electrodes for treatment.

In some embodiments, as shown in FIG. 2B, one or more ultrasound transducers 220 may be located on the inner surface of the one or more splines 204. In some instances, there may be one ultrasound transducer disposed on each spline. In certain instances, there may be more than one ultrasound transducer disposed on each spline. In some instances, selected spline(s) of the one or more splines 204 have one or more ultrasound transducers 220 disposed thereon. In one example, two of four splines 204 include one ultrasound transducers 220 disposed thereon.

In some embodiments, as shown in FIG. 2C, one or more ultrasound transducers 220 may be disposed on the end cap 206 of the electrode assembly 202. In some instances, there may be only one ultrasound transducer 220 disposed on the end cap 206 of the electrode assembly 202. In certain instances, three ultrasound transducers 220 are disposed on the end cap of the electrode assembly 202. In one example, three ultrasound transducers 220 are disposed on the end cap 206 with an equal spacing. In some instances, there may be one or more ultrasound transducer 220 disposed on the distal end 208 of the catheter body 218. By having transducers at both the distal end of the electrode assembly 202 and the distal end of the catheter body 218, in some embodiments, the ultrasound waves may reduce, destruct, and/or prevent microbubble formation in a larger region of the patient's heart compared to having one or more transducers located in the interior cavity 222 of the electrode assembly 202.

Figure 3:
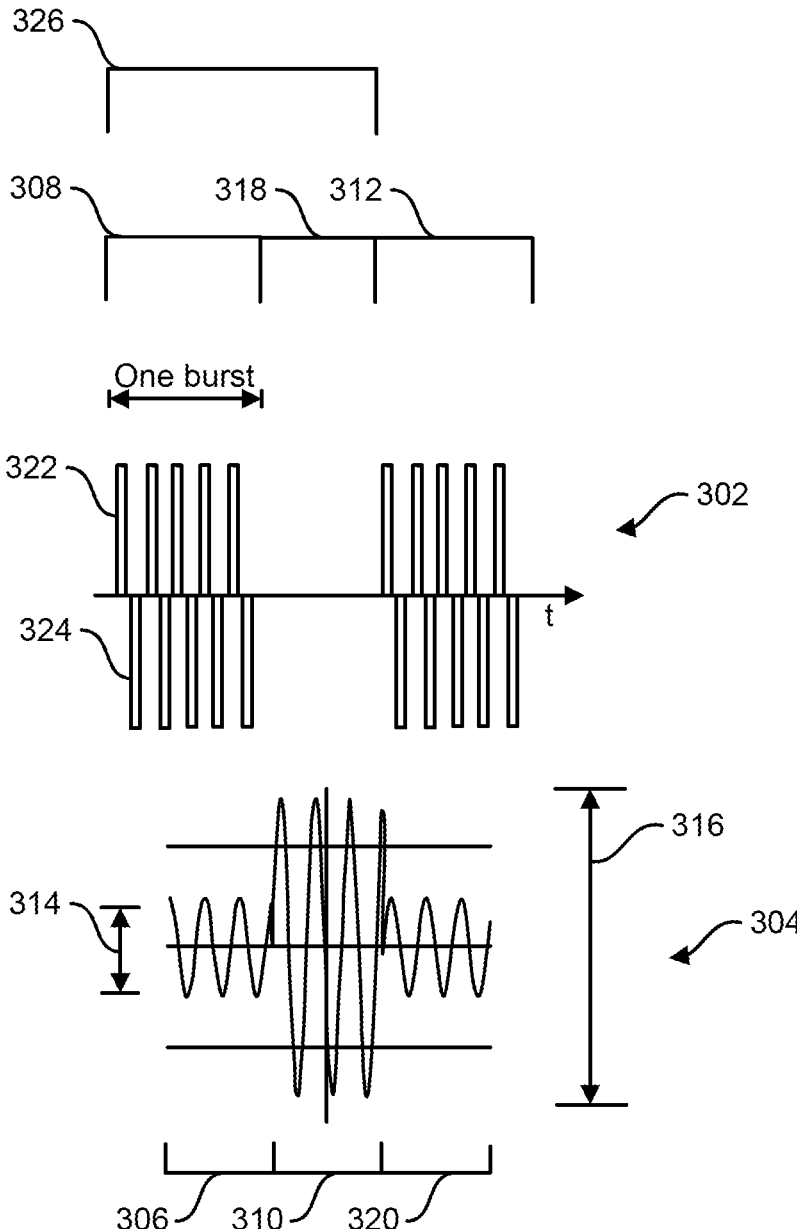
FIG. 3 shows example ultrasound waveforms of the ultrasound transducer during burst, in accordance with embodiments of the subject matter of the disclosure.

FIG. 3 shows ultrasound waveforms 304 produced by the ultrasound transducer (shown in FIG. 2A) synchronizing with a burst train 302 produced by the plurality of electrodes (shown in FIG. 2A). As shown in FIG. 3, one therapy burst 308, also referred to as an electrical pulse sequence, may include a number of positive pulses 322 and a number of negative pulses 324. In one example, the therapy burst 308 has a voltage greater than 500 volt. There may be a quiet period 318 in between each therapy burst 308, 312. In embodiments, a therapy section 326 may include a therapy burst 308 and a quiet period 318. The frequency of the ultrasound waveforms 304 may be between 1-5 MHz. In some instances, the frequency of the ultrasound waveforms may be higher than 5 MHz. In some instances, the frequency of the ultrasound waveforms may be as high as 15 MHz. In some embodiments, the frequency of the ultrasound waveforms 304 between each therapy burst 308, 312 is around 2.9 MHz. In some embodiments, the frequency of the ultrasound waveforms 304 during each therapy burst 308, 312 is around 1 MHz. The magnitude of the ultrasound waveforms 304 may be between 0.5-3.5 MPa. In some embodiments, the magnitude of ultrasound waveforms 304 may be around 0.5 MPa during the therapy bursts 308, 312, and around 3.5 MPa during the quiet period 318 in between the therapy bursts 308, 312. In one example, the ultrasound signals have a voltage around 100 volt.

In some embodiments, the ultrasound transducer is configured to generate a first set of ultrasound signals 306 during a first electrical pulse sequence 308 of the plurality of electrical pulse sequences and generate a second set of ultrasound signals 310 after an end of the first electrical pulse sequence 308 and before a beginning of a second electrical pulse sequence 312, the second electrical pulse sequence 312 being an electrical pulse sequence subsequent to the first electrical pulse sequence 308. In some embodiments, the frequency of the first set of ultrasound signals 306 is lower than the frequency of the second set of ultrasound signals 310. In certain embodiments, the magnitude of the first set of ultrasound signals 306 is lower than the magnitude of the second set of ultrasound signals 310. In some examples, the magnitude of the second set of ultrasound signals 310 is at least three (3) times of the magnitude of the first set of ultrasound signals 306. In certain examples, the magnitude of the second set of ultrasound signals 310 is at least four (4) times of the magnitude of the first set of ultrasound signals 306.

In some instances, during the first electrical pulse sequence 308, the magnitude of the first set of ultrasound signals 306 may be around 0.5 MPa. In some instances, during the quiet period 318, the magnitude of the second set of ultrasound signals 310 may be around 3.5 MPa. In some embodiments, there may be a third set of ultrasound signals 320. As shown, the third set of ultrasound signals 320 may be generated after the beginning of a second electrical pulse sequence 312. In some instances, the magnitude of the third set of ultrasound signals 320 may be the same as the magnitude of the first set of ultrasound signals 306. In some instances, the magnitude of the third set of ultrasound signals 320 may be smaller than the second set of ultrasound signals 310.

As shown, the first set of ultrasound signals 306 has a first average magnitude 314 and the second set of ultrasound signals 310 has a second average magnitude 316. In some instances, the first average magnitude 314 is different from the second average magnitude 316. In some instances, the first average magnitude 314 is lower than the second average magnitude 316. In some embodiments, the magnitude of 314 may be around 0.5 MPa, and the magnitude of 316 may be around 3.5 MPa.

Figure 4:
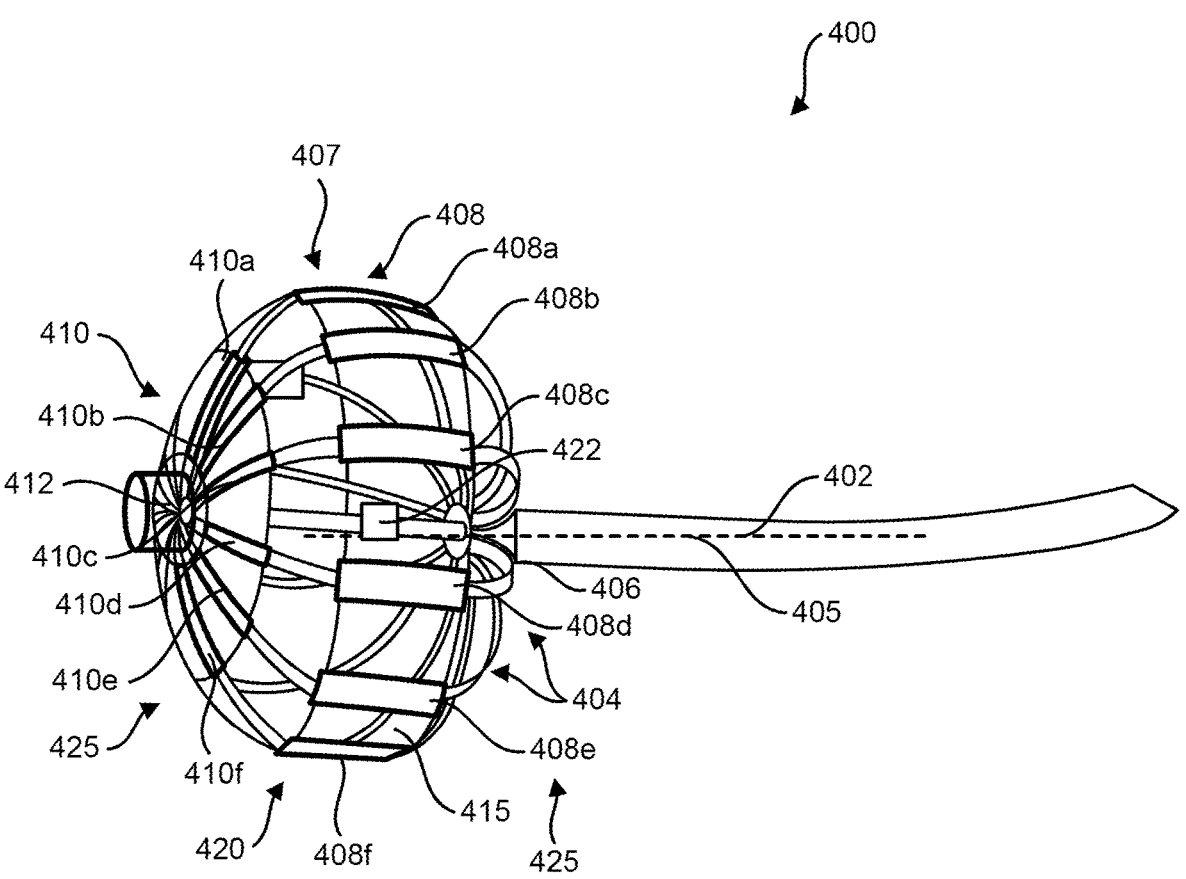
FIG. 4 shows an exemplary electroporation ablation catheter comprising an ultrasound transducer, in accordance with embodiments of the subject matter of the disclosure.

FIG. 4 shows an exemplary electroporation ablation catheter 400 comprising an ultrasound transducer, in accordance with embodiments of the subject matter of the disclosure. As shown in FIG. 4, the catheter 400 includes a catheter shaft 402 with a longitudinal axis 405 and having a distal end 406. As used herein, a longitudinal axis refers to a line passing through the centroid of the cross sections of an object. The catheter 400 further includes an electrode assembly 407. In some embodiments, the electrode assembly 407 extends from the distal end 406 of the catheter shaft 402. In embodiments, the electrode assembly 407 is configured to assume a first collapsed state and a second expanded state. In some cases, the electrode assembly 407 includes an expandable component 420 and a plurality of electrodes 425 disposed on the expandable component 420. The expandable component 420 can be collapsed in the first state and expanded in the second state.

In some embodiments, the electrode assembly 407 includes a plurality of splines 404 forming an interior cavity 415 and an inflatable balloon (not shown) disposed in the cavity 415. In such embodiment, the plurality of splines 404 and the balloon collectively form the expandable component 420.

In some embodiments, the catheter 400 is configured to receive an ablative energy (e.g., electroporation pulse) at the plurality of electrodes 425 and generate an electric field at the electrodes 425. In one embodiment, the electric field has an electric field strength sufficient to ablate a target tissue via irreversible electroporation. In some embodiments, the plurality of electrodes 425 includes a first group of electrodes 408 and a second group of electrodes 410. In some cases, the first group of electrodes 408 disposed at the circumference of the plurality of splines 404 and the second group of electrodes 410 disposed adjacent the distal end 412 of the catheter 400. In some cases, the first group of electrodes 408 are referred to as proximal electrodes, and the second group of electrodes 410 are referred to as distal electrodes, where the distal electrodes 410 are disposed closer to the distal end 412 of the electroporation ablation catheter 400 than the proximal electrodes 408. In some implementations, the electrodes 425 can include a thin film of an electro-conductive or optical ink. The ink can be polymer-based. The ink may additionally comprise materials such as carbon and/or graphite in combination with conductive materials. The electrode can include a biocompatible, low resistance metal such as silver, silver flake, gold, and platinum which are additionally radiopaque.

Each of the electrodes in the first group of electrodes 408 and each of the electrodes in the second group of electrodes 410 is configured to conduct electricity and to be operably connected to a controller and an ablative energy generator (see FIG. 1). In embodiments, one or more of the electrodes in the first group of electrodes 408 and the second group of electrodes 410 includes flex circuits.

Electrodes in the first group of electrodes 408 are spaced apart from electrodes in the second group of electrodes 410. The first group of electrodes 208 includes electrodes 408a-408f and the second group of electrodes 410 includes electrodes 410a-410f. Also, electrodes in the first group of electrodes 408, such as electrodes 408a-408f, are spaced apart from one another and electrodes in the second of electrodes 410, such as electrodes 410a-410f, are spaced apart from one another.

The spatial relationships and orientation of the electrodes in the first group of electrodes 408 and the spatial relationships and orientation of the electrodes in the second group of electrodes 410 in relation to other electrodes on the same catheter 400 is known or can be determined. In embodiments, the spatial relationships and orientation of the electrodes in the first group of electrodes 408 and the spatial relationships and orientation of the electrodes in the second group of electrodes 410 in relation to other electrodes on the same catheter 400 is constant, once the catheter is deployed.

Similar to the ultrasound transducer 220 shown in FIG. 2A, in this balloon catheter, an ultrasound transducer 422 may be placed inside the cavity 415 near the distal end 406 of the catheter 400. The ultrasound transducer 422 is configured to destroy one or more microbubbles that may form during treatment of the patient. Alternatively or additionally, in some embodiments, one or more transducers (not shown) may be disposed on the distal end 412 of the electrode assembly 407, for example, on an end cap. In some embodiments, one or more transducers may be disposed on the distal end 406 of the catheter shaft 400 as well as the distal end 412 of the electrode assembly 412, covering a larger area for reducing, destructing, and/or preventing the microbubble formation in a patient's heart. In some embodiments, the catheter shaft may in include wires for transfer of power and signal control from the first group of electrodes 408, the second group of electrodes 410, and/or one or more ultrasound transducers 422 to a controller (not shown). The controller is configured to receive and send signals to the first group of electrodes 408, the second group of electrodes 410, and/or one or more ultrasound transducers 422 for generation of electroporation pulses and of ultrasound waveforms during therapy sections.

Figure 5:
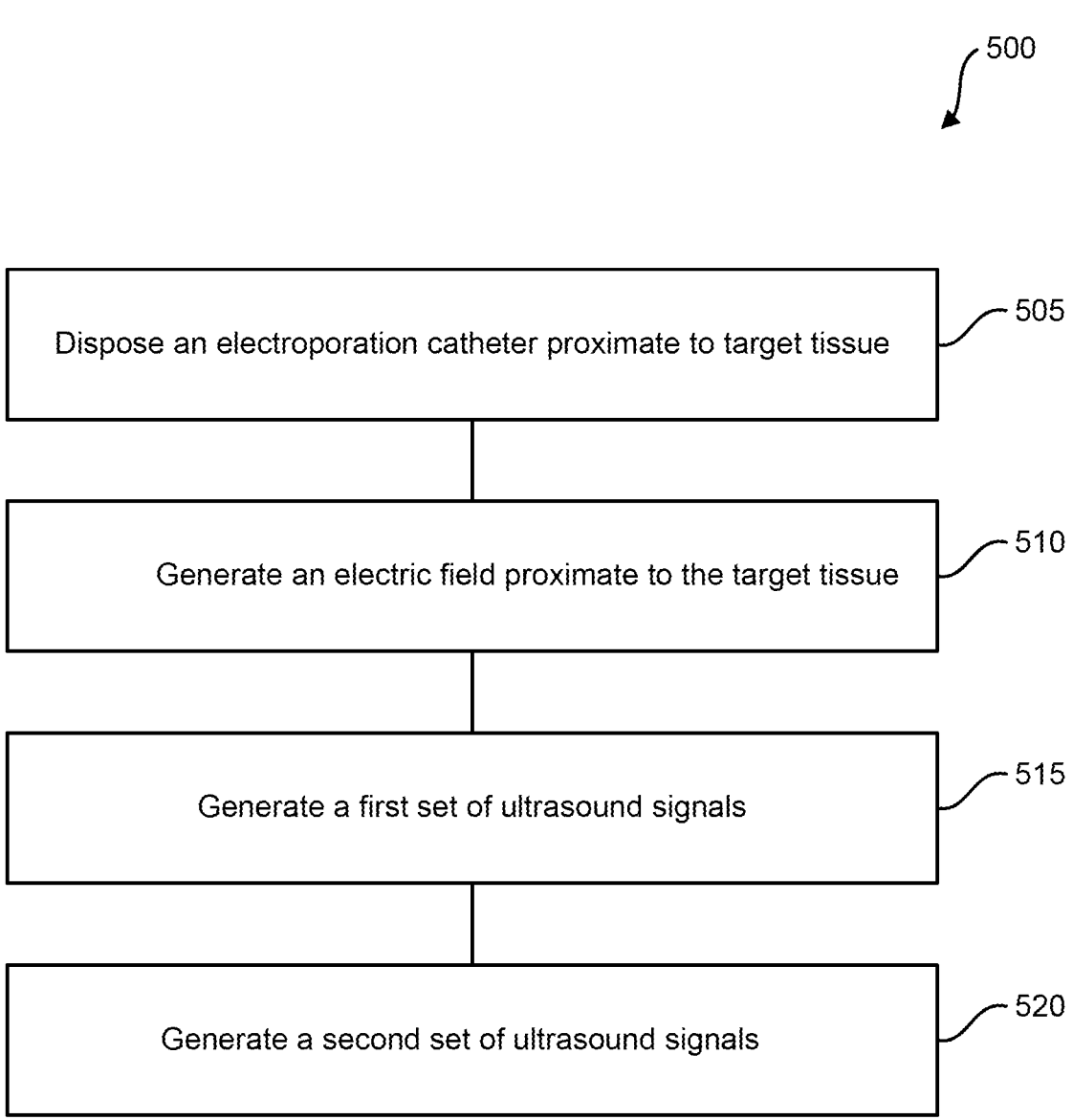
FIG. 5 is a flow chart diagram illustrating a method of reducing or preventing microbubbles formation during cardiac ablation by electroporation, in accordance with embodiments of the subject matter of the disclosure.

FIG. 5 is an example flow diagram illustrating a method 500 of reducing or preventing microbubbles formation during cardiac ablation by electroporation, in accordance with embodiments of the subject matter of the disclosure. Aspects of embodiments of the method 500 may be performed, for example, by an electroporation ablation system/device (e.g., the electrophysiology system 50 depicted in FIG. 1). One or more steps of method 500 are optional and/or can be modified by one or more steps of other embodiments described herein. Additionally, one or more steps of other embodiments described herein may be added to the method 500. As shown in FIG. 5, an electroporation catheter may be disposed proximate to target tissue within a patient (505). In some embodiments, the electroporation catheter includes one or more electrodes and an ultrasound transducer. In some embodiments, the one or more electrodes generate an electric field proximate to the target tissue in response to a plurality of electrical pulse sequences delivered in a plurality of therapy sections, the electric field having electric field strength sufficient to ablate the target tissue via irreversible electroporation (510).

One or more sets of ultrasound signals may be generated to destroy one or more microbubbles that may be formed during treatment of the patient (515, 520). One or more sets of ultrasound signals may include a first set of ultrasound signals and a second set of ultrasound signals. In some instances, the first set of ultrasound signals is generated during a first electrical pulse sequence of the plurality of electrical pulse sequences. In some instances, the second set of ultrasound signals is generated after an end of the first electrical pulse sequence and before a beginning of a second electrical pulse sequence by an ultrasound transducer. In some instances, the first set of ultrasound signals has a first average magnitude, the second set of ultrasound signals has a second average magnitude. In some examples, the first average magnitude is different from the second average magnitude. In certain examples, the first average magnitude is lower than the second average magnitude.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. An electroporation ablation catheter, comprising:

an electrode assembly comprising:

one or more electrodes configured to generate electric fields in target tissue in response to a plurality of electrical pulse sequences delivered in a plurality of therapy sections to effect electroporation of the target tissue; and an ultrasound transducer configured to generate a first set of ultrasound signals concurrently with a first electrical pulse sequence of the plurality of electrical pulse sequences and generate a second set of ultrasound signals after an end of the first electrical pulse sequence and before a beginning of a second electrical pulse sequence, the second electrical pulse sequence being an electrical pulse sequence subsequent to the first electrical pulse sequence;

wherein the first set of ultrasound signals has a first average magnitude;

wherein the second set of ultrasound signals has a second average magnitude; and wherein the first average magnitude is different from the second average magnitude.

2. The electroporation ablation catheter of claim 1, wherein the first average magnitude is lower than the second average magnitude.

3. The electroporation ablation catheter of claim 1, wherein the electrode assembly further comprises an internal component disposed at an interior cavity of the electrode assembly; and wherein the ultrasound transducer is disposed on the internal component.

4. The electroporation ablation catheter of claim 1, further comprising one or more wirings to power up the ablation catheter and to control at least one of a magnitude and frequency of the first set and the second set of ultrasound signals.

5. The electroporation ablation catheter of claim 1, wherein the electrode assembly further comprises a plurality of splines;

wherein the ultrasound transducer comprises one ultrasound transducer disposed on one of the plurality of splines.

6. The electroporation ablation catheter of claim 1, wherein the first set of ultrasound signals has a first average frequency, wherein the second set of ultrasound signals has a second average frequency, wherein the first average frequency is different from the second average frequency.

7. An electroporation ablation catheter, comprising:

an elongated shaft having a distal end; and an electrode assembly coupled to the distal end, the electrode assembly comprising:

one or more electrodes configured to generate electric fields to effect electroporation in target tissue in response to a plurality of electrical pulse sequences delivered in a plurality of therapy sections, the electrode assembly configurable in an expanded configuration to define an interior cavity;

an ultrasound transducer configured to generate a first set of ultrasound signals during a first electrical pulse sequence of the plurality of electrical pulse sequences and generate a second set of ultrasound signals after an end of the first electrical pulse sequence and before a beginning of a second electrical pulse sequence, the second electrical pulse sequence being an electrical pulse sequence subsequent to the first electrical pulse sequence; and an internal component extending from the distal end of the shaft and disposed in the interior cavity of the electrode assembly; and wherein the ultrasound transducer is disposed on the internal component.

8. The electroporation ablation catheter of claim 7, wherein the first set of ultrasound signals has a first average magnitude, the second set of ultrasound signals has a second average magnitude; and wherein the first average magnitude is different from the second average magnitude.

9. The electroporation ablation catheter of claim 8, wherein the first average magnitude is lower than the second average magnitude.

10. The electroporation ablation catheter of claim 7, wherein the internal component comprises a deployment shaft.

11. The electroporation ablation catheter of claim 10, further comprising:

a catheter shaft having a proximal end and a distal end;

wherein the electrode assembly extends from the distal end of the catheter shaft; and wherein the deployment shaft extends from the distal end of the catheter shaft.

12. The electroporation ablation catheter of claim 7, wherein the electrode assembly further comprises a plurality of splines;

wherein the ultrasound transducer comprises one ultrasound transducer disposed on one of the plurality of splines.

13. The electroporation ablation catheter of claim 12, wherein at least a part of the plurality of splines form an interior cavity.

14. The electroporation ablation catheter of claim 7, wherein the first set of ultrasound signals has a first average frequency, wherein the second set of ultrasound signals has a second average frequency, wherein the first average frequency is different from the second average frequency.

15. A method of reducing microbubbles formation during cardiac ablation, comprising:

disposing an electroporation catheter proximate to target tissue, the electroporation catheter comprising one or more electrodes and an ultrasound transducer;

generating an electric field, by the one or more electrodes, proximate to the target tissue in response to a plurality of electrical pulse sequences delivered in a plurality of therapy sections, the electric field having electric field strength sufficient to ablate the target tissue via irreversible electroporation;

generating, by the ultrasound transducer, a set of ultrasound signals, wherein the set of ultrasound signals comprises a first set of ultrasound signals and a second set of ultrasound signals.

16. The method of claim 15, wherein the first set of ultrasound signals is generated during a first electrical pulse sequence of the plurality of electrical pulse sequences.

17. The method of claim 15, wherein the second set of ultrasound signals is generated after an end of the first electrical pulse sequence and before a beginning of a second electrical pulse sequence.

18. The method of of claim 15, wherein the first set of ultrasound signals has a first average magnitude;

wherein the second set of ultrasound signals has a second average magnitude; and wherein the first average magnitude is different from the second average magnitude.

\* \* \* \* \*